United States Patent
Tarbet et al.

(10) Patent No.: US 11,614,386 B2
(45) Date of Patent: Mar. 28, 2023

(54) SYSTEM AND METHOD OF MONITORING TISSUE SAMPLES TO BE PROCESSED BY A TISSUE PROCESSOR

(71) Applicant: LEICA BIOSYSTEMS MELBOURNE PTY LTD, Mount Waverly (AU)

(72) Inventors: Fiona Mary Tarbet, Box Hill North (AU); Donnchadh Oh-Ainle, Prahran (AU)

(73) Assignee: LEICA BIOSYSTEMS MELBOURNE PTY LTD, Mount Waverley (AU)

( * ) Notice: Subject to any disclaimer, the term of this patent is extended or adjusted under 35 U.S.C. 154(b) by 446 days.

(21) Appl. No.: 16/621,148

(22) PCT Filed: Aug. 22, 2018

(86) PCT No.: PCT/AU2018/050890
§ 371 (c)(1),
(2) Date: Dec. 10, 2019

(87) PCT Pub. No.: WO2019/036758
PCT Pub. Date: Feb. 28, 2019

(65) Prior Publication Data
US 2021/0140857 A1    May 13, 2021

Related U.S. Application Data

(60) Provisional application No. 62/548,651, filed on Aug. 22, 2017.

(51) Int. Cl.
*G01N 1/31* (2006.01)
*G16H 40/20* (2018.01)
(Continued)

(52) U.S. Cl.
CPC ......... *G01N 1/31* (2013.01); *G01N 35/00732* (2013.01); *G01N 35/00871* (2013.01);
(Continued)

(58) Field of Classification Search
CPC .................................. G16H 40/20; G16J 10/40
(Continued)

(56) References Cited

U.S. PATENT DOCUMENTS 9,691,043 B2 *  6/2017  Gurney ................... G16H 70/60
10,871,425 B2 * 12/2020  Barnes ................... G06T 7/0014
(Continued)

FOREIGN PATENT DOCUMENTS

EP    3 339 866 A1    6/2018
EP    3 438 639 A1    2/2019
(Continued)

OTHER PUBLICATIONS ip.com search.*
(Continued)

*Primary Examiner* — Allyson N Trail
(74) *Attorney, Agent, or Firm* — Sughrue Mion, PLLC

(57) ABSTRACT

A system for monitoring tissue samples to be processed by a tissue processor for a histopathology workflow, the system including: a scanner associated with the tissue processor arranged to scan an electronic sample identifier of at least one tissue sample to be processed by the tissue processor; an input module arranged to receive tissue processor workflow data indicative of a tissue processor workflow for the at least one tissue sample to be processed by selected ones of a plurality of processing stations in the tissue processor used for processing the at least one tissue sample; a monitoring module arranged to monitor properties of the at least one tissue sample processed at each of the selected ones of the processing stations and to record the properties of the at least
(Continued)

one tissue sample in association with the electronic sample identifier in a sample record for the tissue processor workflow; and an output module arranged to output the sample record to one or more laboratory instruments for further processing the at least one tissue sample in a histopathology workflow. A tissue processor for processing tissue samples for a histopathology workflow is also provided. A method of monitoring tissue samples to be processed by a tissue processor for a histopathology workflow is also provided.

19 Claims, 5 Drawing Sheets

(51) Int. Cl.
  G16H 10/40 (2018.01)
  G01N 35/00 (2006.01)
(52) U.S. Cl.
  CPC ............. G16H 10/40 (2018.01); G16H 40/20 (2018.01); *G01N 2035/00752* (2013.01)
(58) Field of Classification Search
  USPC ...................................................... 435/40.52
  See application file for complete search history.

(56) References Cited

U.S. PATENT DOCUMENTS

| | | | |
|---|---|---|---|
| 11,071,978 B2 * | 7/2021 | Crum | ..................... B01L 3/502 |
| 2006/0159325 A1 | 7/2006 | Zeineh et al. | |
| 2008/0113440 A1 | 5/2008 | Gurney et al. | |
| 2011/0045565 A1 | 2/2011 | Sanders et al. | |
| 2012/0163680 A1 | 6/2012 | Lefebvre | |
| 2012/0197660 A1 * | 8/2012 | Prodanovich | .......... G16H 10/40 235/494 |
| 2014/0188545 A1 | 7/2014 | Chirica et al. | |
| 2015/0335248 A1 * | 11/2015 | Huang | ................... G01N 21/65 702/19 |
| 2018/0173851 A1 † | 6/2018 | Visinoni | |
| 2019/0033179 A1 † | 1/2019 | Minuti | |
| 2020/0141920 A1 * | 5/2020 | Glazier | .................. G01N 33/49 |

FOREIGN PATENT DOCUMENTS

| | | |
|---|---|---|
| EP | 3 438 639 B1 | 10/2019 |
| EP | 3 339 866 B1 | 4/2020 |
| JP | 2012-514201 A | 6/2012 |
| JP | 2012-141287 A | 7/2012 |
| JP | 2013-502560 A | 1/2013 |
| WO | 2010/078240 A1 | 7/2010 |
| WO | 2011/020574 A1 | 2/2011 |
| WO | 2016/120224 A1 | 8/2016 |

OTHER PUBLICATIONS

Written Opinion of the International Searching Authority of PCT/AU2018/050890 dated Oct. 9, 2018.
International Search Report of PCT/AU2018/050890 dated Oct. 9, 2018.
Communication dated Mar. 2, 2022, issued by the Intellectual Property Office of India in application No. 201917051707.
Communication dated Jan. 28, 2021, from the European Patent Office in application No. 18848903.3.
Office Action dated Jul. 12, 2022 from the Korean Intellectual Property Office in KR Application No. 10-2019-7037711.
Office Action dated Jun. 14, 2022 in Japanese Application No. 2020-501196.
Third Party Observation issued Apr. 5, 2022 in European Application No. 18848903.3.
Communication dated Jun. 14, 2022 from the Japanese Patent Office in Japanese Application No. 2020-501196.
Office Action dated Nov. 7, 2022 issued by the European Patent Office in European Application No. 18848903.3.
Office Action dated Oct. 25, 2022 issued by the Japanese Patent Office in Japanese Application No. 2020-501196.

\* cited by examiner
† cited by third party

SYSTEM AND METHOD OF MONITORING TISSUE SAMPLES TO BE PROCESSED BY A TISSUE PROCESSOR

This application is a National Stage of International Application No. PCT/AU2018/050890 filed Aug. 22, 2018, claiming priority based on U.S. Provisional Patent Application No. 62/548,651 filed on 22 Aug. 2017, the contents of which are to be taken as incorporated herein by this reference.

TECHNICAL FIELD

The present invention relates to a system and method of monitoring tissue samples to be processed by a tissue processor for a histopathology workflow. The present invention is of particular but not exclusive application in monitoring and recording properties of tissue samples being processed in association with an electronic sample identifier in a sample record, outputting the sample record for use by laboratory instruments further processing the tissue samples in the histopathology workflow.

BACKGROUND OF INVENTION

Biological tissue samples, in particular histological tissue samples, are often required in the fields of human and veterinary medicine, in particular as microscopic prepared specimens for the assessment of cells and their environment. For microscopic inspection, thin sections of the tissue sample must be prepared for assessment under the microscope, in incident or transmitted light, by an expert.

The production of thin sections, for example using a microtome, requires that the tissue sample have a certain strength so that thin, transparent sections having a thickness on the order of micrometres can be produced using a knife. For this purpose, the tissue sample must first pass through a treatment process in which it is fixed, dehydrated, cleared, and then infiltrated with a carrier material, preferably melted paraffin. These processes are often performed successively in a single unit called a "tissue processor"; this tissue processor includes for this purpose a closable process chamber called a "retort" that receives the various reagents, in particular process media, for carrying out the process steps at a suitable temperature and pressure.

These processes for processing the tissue samples in the tissue processor are generally provided as a tissue processor workflow. The tissue processor workflow defines the processes to be applied by selected laboratory stations in the tissue processor, such as the retort. Also, where the tissue sample is to be analysed for histopathological or histological assessment, the tissue processor workflow forms part of a histopathology workflow.

For example, immunohistochemical staining and in situ nucleic acid analysis are existing tools used in histological diagnosis and the study of tissue morphology that are part of a typical histopathology workflow. Immunohistochemical staining relies on the specific binding affinity of antibodies with epitopes in tissue samples, and the increasing availability of antibodies which bind specifically with unique epitopes present only in certain types of diseased cellular tissue. Immunohistochemical staining involves a series of treatment steps conducted on a tissue sample (typically a section) mounted on a glass slide to highlight, by selective staining, certain morphological indicators of disease states.

Typical treatment steps for immunohistochemical staining include pretreatment of the tissue sample using the tissue processor to reduce non-specific binding, antibody treatment and incubation, enzyme labelled secondary antibody treatment and incubation, substrate reaction with the enzyme to produce a fluorophore or chromophore highlighting areas of the tissue sample having epitopes binding with the antibody, counterstaining, and the like. Between each treatment step, the tissue sample must be rinsed to remove unreacted residual reagent from the prior step. Most treatment steps involve a period of incubation typically conducted at ambient temperature of around 25° C. up to around 40° C., while cell conditioning steps are typically conducted at somewhat higher temperatures, e.g. 90° C. to 100° C. In-situ DNA analysis relies upon the specific binding affinity of probes (DNA binding proteins) with unique nucleotide sequences in cell or tissue samples and similarly involves a series of process steps, with a variety of reagents and process temperature requirements. Some specific reactions involve temperatures up to 120° C. to 130° C. Accordingly, the pretreatment of tissue samples in a tissue processor introduces a large amount of variability which will likely affect the further processing of the tissue samples in the other laboratory instruments in the remainder of the histopathology workflow.

Attempts have been made to automate some of the laboratory instruments used to process tissue samples in a histopathological workflow. In an existing application, for instance, an automated tissue sample staining apparatus is employed to treat tissue samples disposed on slides for immunologic applications. In this example, an automated staining apparatus implements a number of laboratory modules in a single instrument to treat tissue samples using reagents and to then stain the samples disposed on slides. In the example, the treatment of samples using such an apparatus includes configuring one or more robots to dunk the slides in a dewaxing solution and then dispensing reagents to the samples on the slides in a predetermined sequence according to a staining protocol. The automated tissue sample staining apparatus, however, has limited or no knowledge of the prior tissue sample processing steps which can, in some instances, negatively affect the quality of stain.

Further, while most modern laboratory instruments are automated in some way and computer control is becoming common place, each instrument may have a unique operating system and use different data schema and control signals to communicate.

SUMMARY OF INVENTION

Accordingly, one aspect of the present invention provides a system for monitoring tissue samples to be processed by a tissue processor for a histopathology workflow, the system including: a scanner associated with the tissue processor arranged to scan an electronic sample identifier of at least one tissue sample to be processed by the tissue processor; an input module arranged to receive tissue processor workflow data indicative of a tissue processor workflow for the at least one tissue sample to be processed by selected ones of a plurality of processing stations in the tissue processor used for processing the at least one tissue sample; a monitoring module arranged to monitor properties of the at least one tissue sample processed at each of the selected ones of the processing stations and to record the properties of the at least one tissue sample in association with the electronic sample identifier in a sample record for the tissue processor workflow; and an output module arranged to output the sample record to one or more laboratory instruments for further processing the at least one tissue sample in a histopathology workflow.

In this aspect, the system includes the modules arranged to be used with respect to a tissue processor for a histopathology workflow for monitoring the tissue samples processed by the tissue processor. One or more of the modules could be arranged, for instance, in a client-server arrangement. For example, the input module, monitoring module and output module are provided by a server in data communication with one or more tissue processors, and the scanner may be co-located with each tissue processor.

Another aspect of the present invention provides a tissue processor for processing tissue samples for a histopathology workflow, the tissue processor including: a scanner arranged to scan an electronic sample identifier of at least one tissue sample to be processed by the tissue processor; a plurality of processing stations arranged to process the at least one tissue sample; an input module arranged to receive tissue processor workflow data indicative of a tissue processor workflow for the at least one tissue sample to be processed by selected ones of the plurality of processing stations; a monitoring module arranged to monitor properties of the at least one tissue sample processed at each of the selected ones of the processing stations and to record the properties of the at least one tissue sample in association with the electronic sample identifier in a sample record for the tissue processor workflow; and an output module arranged to output the sample record to one or more laboratory instruments for further processing the at least one tissue sample in a histopathology workflow.

In this aspect, the tissue processor incorporates the modules used to monitor tissue samples being processed for a histopathology workflow.

The plurality of processing stations arranged to process the at least one tissue sample may include a retort for processing tissue samples with different reagents. It will be appreciated by those persons skilled in the art that the retort can be used to implement a number of processing steps that could otherwise be implemented in a number of processing stations, such as fixing with formalin, dehydrating with alcohol, clearing with Xylene, and adding Paraffin to the samples.

In some embodiments, the sample record further includes, in association with the electronic sample identifier, the tissue processor workflow data indicative of the tissue processor workflow for the at least one tissue sample. Also, in some embodiments the sample record further includes, in association with the electronic sample identifier, expected properties of the at least one tissue sample based on the tissue processor workflow for the at least one tissue sample.

In some embodiments, the system further includes one or more sensors associated with each of the plurality of processing stations in the tissue processor arranged to sense said properties of the at least one tissue sample being processed. In some embodiments, the tissue processor further includes one or more sensors associated with each of the plurality of processing stations in the tissue processor arranged to sense said properties of the at least one tissue sample being processed. Preferably, the properties of the at least one tissue sample being processed include: fixation period, tissue thickness, tissue type, protocol step, protocol duration, reagent concentration, reagent lot number, retort temperature, cycle times, and reagent carryover. Some properties may also be derived from sensed properties. Concentration of reagent that will process tissue is derived from a calculation of Carryover. The Carryover is defined as the amount of reagent brought forward from the previous steps in the process and from the number of cassettes, baskets, tissues and biopsy restraints in the current processing run. This is calculated from both instrument inputs and user inputs.

In some embodiments, the at least one tissue sample to be processed by the tissue processor is provided in a cassette, and the electronic sample identifier includes a cassette identifier. Further, the cassette may be provided in a basket, and the electronic sample identifier may further include a basket identifier. Still further, the electronic sample identifier (e.g. the cassette or basket identifier) may include a barcode tag. For example, the at least one sample may be associated with the basket identifier in these embodiments at grossing of the at least one sample. Preferably, the barcode tag is a 2-Dimensional datamatrix numerical barcode with human readable text. Alternatively, the basket identifier is a Radio Frequency Identification Technology (RFID) tag.

It will be appreciated by those persons skilled in the art that other electronic readable identifiers could be used, such as, but are not limited to: printed text, a bar code (1, 2 or 3 dimensional), data glyphs, Optical Character Recognition (OCR) code, integrated circuit disposed on the identifier or identifier support, Radio Frequency Identification Technology (RFID) tags and e-ink. The electronic readable identifier may also be communicatively coupled (through a communications infrastructure such as the internet, Wi-Fi or other communication network, Bluetooth, RFID, cellular and others) with the tissue processor or other monitoring device.

In some embodiments, the system can log the software and/or sensor data used to automate tissue processing and use it to provide information to histopathology lab users.

In an example, a tissue sample is grossed by being cut up and placed into a cassette and the cassette is then placed in a basket. A user of the tissue processor can then associate the basket with a tissue processor workflow for the tissue sample when loading it into the basket and then into the tissue processor. The tissue processor receives the tissue processor workflow data and scans the electronic sample identifier in the form of a basket barcode tag using the scanner to identify the sample being processed according to the tissue processor workflow. As above, the properties of the tissue sample being processed are then recorded in association with the electronic sample identifier in a sample record for outputting to one or more further laboratory instruments for further processing the tissue sample in a histopathology workflow.

The tissue processing protocol and reagents form part of the validation record for advanced staining optimisation in a laboratory. In an example, the advanced staining process is altered based on the sample record to re-validate staining techniques based on processing outputs, such as the macroscopic and/or microscopic appearance or some other property of the tissue (e.g. tissue quality).

In some embodiments, the tissue processor further includes a display so that information indicative of the sample record is displayed on the display to a user of the tissue processor. Alternatively, the system may also further include a display associated with the server so that information indicative of the sample record is displayed to a user monitoring tissue samples being processed by one or more tissue processors. In these embodiments, the user can visually determine whether the tissue processing met the requisite standards of processing.

Preferably, the sample record is provided as a collated report that can be filtered by a user and viewed by the user on the tissue processor. Also, in some embodiments, the sample record is outputted via USB in a CSV format for use by the other laboratory instruments in the histopathology workflow. Further, the sample record may be outputted using a common architecture for the laboratory instruments, such as Laboratory Information System (LIS). It will be appreciated by those persons skilled in the art that other options may be provided to package the sample record and to allow users to export it. The sample record can be provided as raw data, tabulated data, collated as reports, have provision for filtering (e.g. filtering by date, by user, by event etc.), and can be in multiple formats (e.g. html, csv files for use in excel, pdf etc.). Users can access the sample record via multiple channels; for example, it can be viewed on an instrument display, manually exported by the user (e.g. via USB or other connection type) or automatically accessed (e.g. via an Ethernet for use in a LIS). It will also be appreciated that the typical data entry, data logging and sample tracking (e.g. barcoded samples at grossing), tissue processing instruments, of the type described above, do not have this provision. As a result, processes and controls are manual, making it difficult to track patient samples through the tissue processing process and making any troubleshooting (e.g. in the event of suboptimal tissue processing) difficult and impractical.

Another aspect of the present invention provides a method of monitoring tissue samples to be processed by a tissue processor for a histopathology workflow, the method including: receiving from a scanner associated with the tissue processor, an electronic sample identifier of at least one tissue sample to be processed by the tissue processor; receiving tissue processor workflow data indicative of a tissue processor workflow for the at least one tissue sample to be processed by selected ones of a plurality of processing stations in the tissue processor used for processing the at least one tissue sample; monitoring properties of the at least one tissue sample processed at each of the selected ones of the processing stations; recording the properties of the at least one tissue sample in association with the electronic sample identifier in a sample record for the tissue processor workflow; and outputting the sample record to one or more laboratory instruments for further processing the at least one tissue sample in a histopathology workflow.

BRIEF DESCRIPTION OF DRAWINGS

The invention will now be described in greater detail with reference to the accompanying drawings in which like features are represented by like numerals. It is to be understood that the embodiments shown are examples only and are not to be taken as limiting the scope of the invention as defined in the claims appended hereto. The embodiments are described with reference to the accompanying drawings, in which:

DETAILED DESCRIPTION

Embodiments of the invention are discussed herein by reference to the drawings which are not to scale and are intended merely to assist with explanation of the invention.

Figure 1:
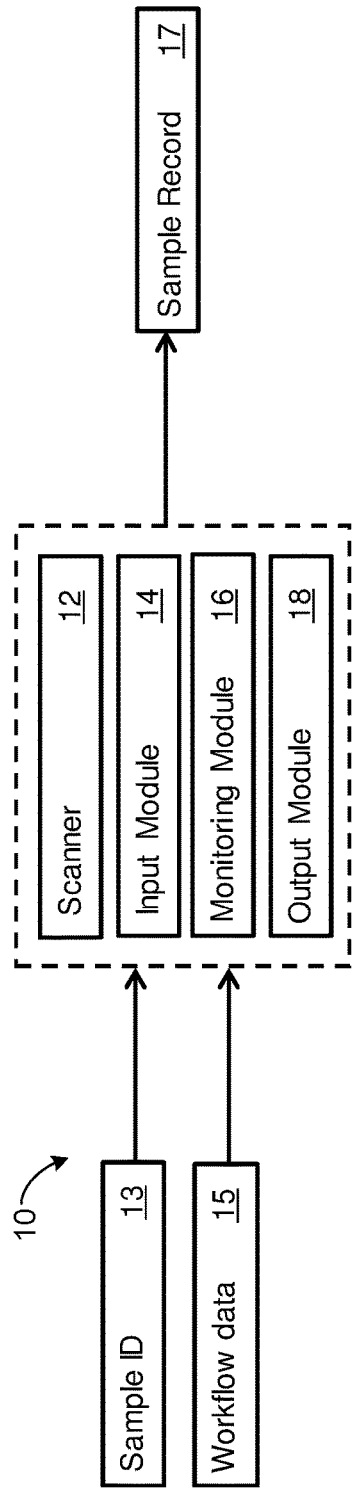
FIG. 1 is a schematic view of a system for monitoring tissue samples to be processed by a tissue processor for a histopathology workflow according to an embodiment of the present invention.

An embodiment of a system 10 for monitoring tissue samples to be processed by a tissue processor for a histopathology workflow is shown in FIG. 1. The system 10 includes a scanner 12 associated with a tissue processor that is arranged to scan an electronic sample identifier 13 of at least one tissue sample to be processed by the tissue processor. As discussed, the system 10 could be implemented in a client-server arrangement, with a number of modules for monitoring the tissue samples being processed by the tissue processor being implemented by the server. In this way, the system 10 can be used to monitor tissue samples processed by many tissue processors and can be applied to existing tissue processors in data communication with the server over a network.

These modules implemented by the server include: an input module 14 arranged to receive tissue processor workflow data 15 indicative of a tissue processor workflow for the at least one tissue sample to be processed by selected ones of a plurality of processing stations in the tissue processor used for processing the at least one tissue sample. That is, the tissue processor includes a number of processing stations discussed in more detail below that are arranged to process the tissue sample according to the tissue processor workflow.

The modules also include a monitoring module 16 arranged to monitor properties of the at least one tissue sample processed at each of the selected ones of the processing stations according to the tissue processor workflow, and to record the properties of the at least one tissue sample in association with the electronic sample identifier 13 in a sample record 17 for the tissue processor workflow. Further, an output module 18 is arranged to output the sample record 17 to one or more laboratory instruments for further processing the at least one tissue sample in a histopathology workflow.

Figure 5:
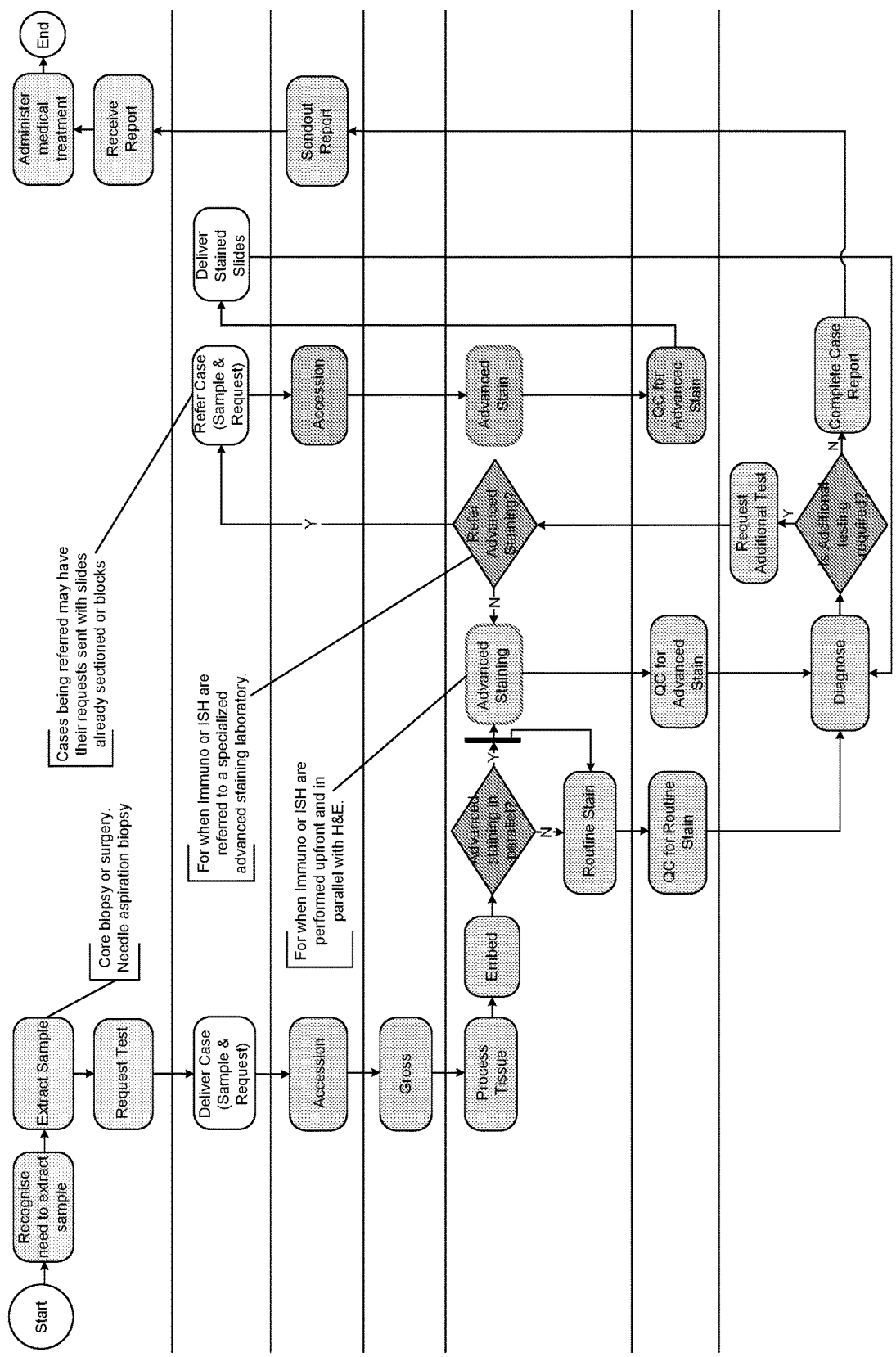
FIG. 5 is a flow chart of a sample being processed by laboratory instruments in a system for treating tissue samples according to an embodiment of the present invention.

FIG. 5 shows an example of a histopathology workflow. Here it can be seen that the steps of grossing tissue samples, processing the tissue samples using a tissue processor, and embedding the tissue samples occur just before the advanced staining step. Accordingly, it will be appreciated that the quality of the tissue processing steps affect the advanced staining and thus diagnosis of the tissue samples in a histopathological workflow.

Figure 2:
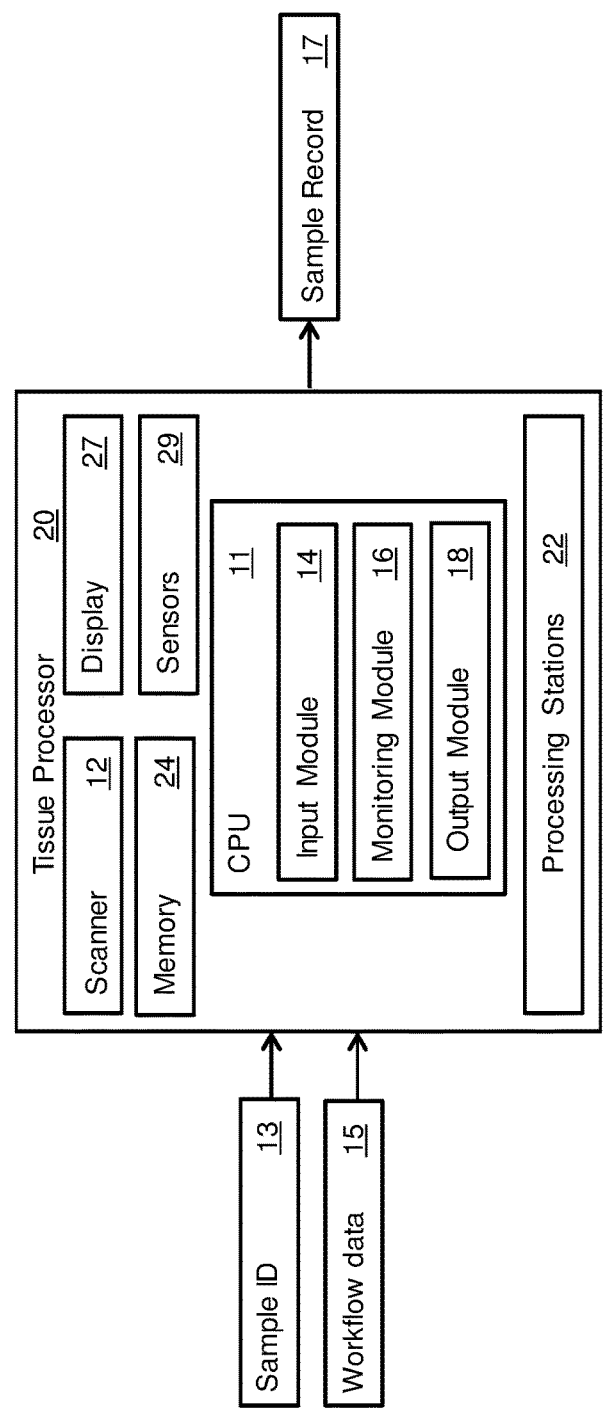
FIG. 2 is another schematic view of a system for monitoring tissue samples to be processed by a tissue processor for a histopathology workflow according to an embodiment of the present invention.

FIG. 2 shows an alternative embodiment of a tissue processor 20 incorporating the above mentioned modules to monitor tissue samples being processed by the tissue processor 20 for a histopathology workflow. That is, the tissue processor 20 includes a scanner 12, co-located with the tissue processor 20, arranged to scan an electronic sample identifier 13 of at least one tissue sample to be processed by the tissue processor 20.

For example, the electronic sample identifier is a barcode tag. In one embodiment, the barcode tag is applied to a basket containing tissue samples that were cut up and placed into a cassette which was placed into a basket for batch processing of the samples in the cassette. In another embodiment, the identifier is applied to a cassette. Further, the cassette can also have a cassette identifier in addition to the basket identifier to further identify the samples being processed by the tissue processor 20.

The tissue processor 20 includes a plurality of processing stations 22 that are arranged to process the at least one tissue sample according to the tissue processor workflow. One of the processing stations 22 is a retort for processing tissue samples with different reagents. The tissue processor workflow includes details of which ones of these stations 22 are to be used to process the samples and in which order. These stations 22 will be described in more detail below.

The tissue processor 20 also includes a CPU 11 (or other microprocessor) configured to implement the above mentioned modules to monitor the tissue samples being processed by the tissue processor 20. The CPU 11 is configured to perform these modules by executing program code stored on a memory 24 for each of the modules. It will be appreciated by those persons skilled in the art that the client-server arrangement described above also uses program code to implement the modules and this code may be stored in a memory in data communication with a server processor.

Specifically, the modules implemented by the CPU 11 of the tissue processor 20 shown in FIG. 2 include: an input module 14 arranged to receive tissue processor workflow data 15 indicative of a tissue processor workflow for the samples being processed by selected ones of the plurality of processing stations 22. While the samples are being processed by the tissue processor 20, a monitoring module 16 is arranged to monitor properties of the tissue samples processed at each of the processing stations 22 and to record these properties in association with the electronic sample identifier 13 in a sample record 17 for the tissue processor workflow. Further, the tissue processor 20 includes an output module 18 arranged to output the sample record 17 to one or more laboratory instruments for further processing the tissue sample in a histopathology workflow.

Figure 3:
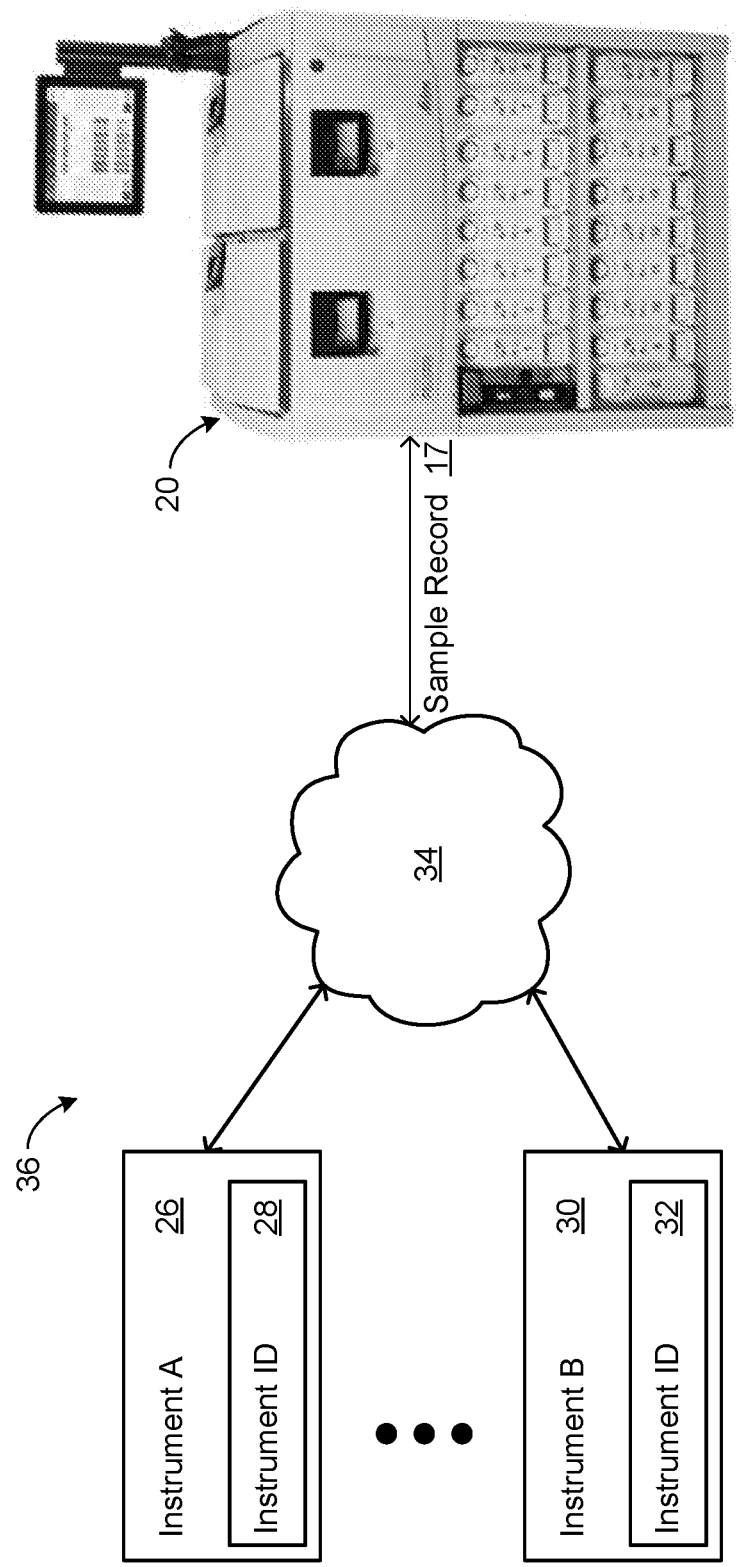
FIG. 3 is a schematic view of a system for treating tissue samples according to an embodiment of the present invention.

An example of another laboratory instrument for further processing a tissue sample in a histopathological workflow includes an automated tissue staining apparatus. FIG. 3 shows a representation of the tissue processor 20 in data communication with instrument A 26 (e.g. automated tissue staining apparatus), having instrument ID 28, and instrument B 30, having instrument ID 32, over a network 34, the components forming a system 36 for treating tissue samples according to an embodiment of the invention. The sample record 17 is communicated over the network 34 in a format that is understood by the laboratory instruments A 26 and B 30 for further processing the tissue sample in a histopathology workflow. The sample record 17 includes, in association with the electronic sample identifier, the tissue processor workflow data indicative of the tissue processor workflow for the at least one tissue sample. The sample record 17 also includes expected properties of the at least one tissue sample based on the tissue processor workflow for the at least one tissue sample. These properties are used by say the automated tissue staining apparatus (e.g. instrument A 26) to modify its workflow to ensure a higher quality stain.

Furthermore, the sample record 17 is used as a troubleshooting tool to determine if there are any reasons, due to say processing or reagent issues, for errors in the tissue processing occurring. It is also used as a Quality Control (QC) record that may be required to be shown on audit.

Figure 4:
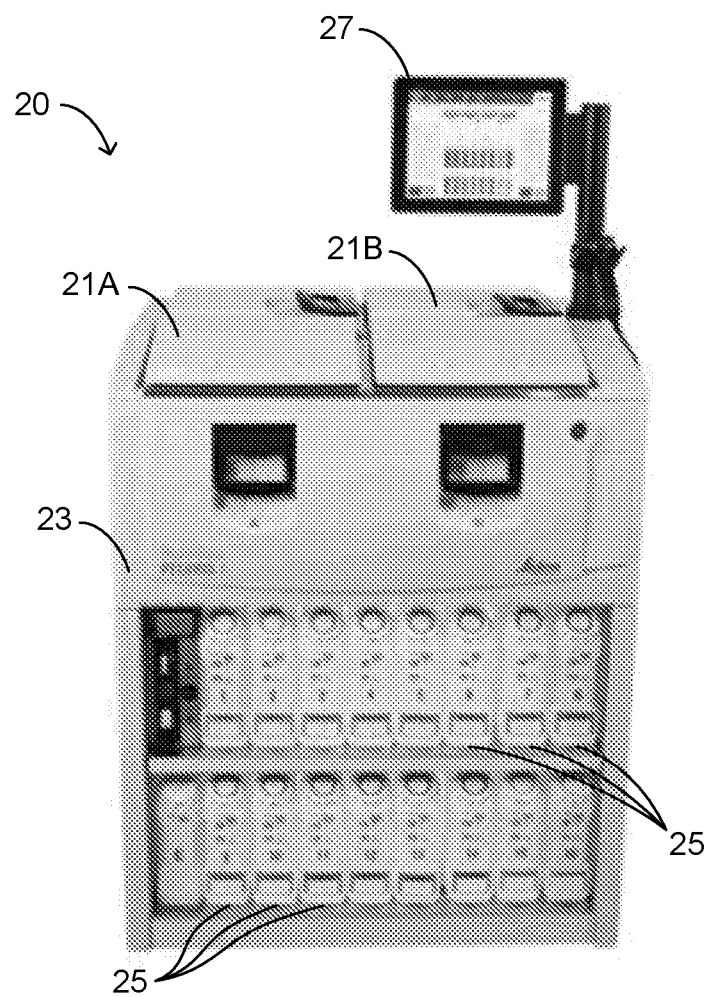
FIG. 4 is a representation of a tissue processor for a histopathology workflow according to an embodiment of the present invention.

FIG. 4 shows an embodiment of the above described tissue processor 20 and its processing stations 22. The tissue processor 20 includes two processing stations 22 as retorts 21A and 21B for processing tissue samples with different reagents simultaneously. In the retorts 21A and 21B, tissue samples pass through multiple process steps. It will be appreciated by those persons skilled in the art that when the retorts 21A and 21B are performing these different steps, the retorts 21A and 21B themselves form different processing stations 22.

One such process is a fixing process, in which formalin is typically used. This process preferably occurs first in the tissue processing workflow. A dehydration process is then accomplished, using alcohol solutions of various degrees of purity. In a subsequent clearing process, alcohol residues are removed from the tissue samples and the tissue samples are prepared for the uptake of carrier material. Xylene or a similar medium is often used in this clearing process. Paraffin or wax of various compositions is preferably suitable as a carrier material. Individual or multiple process steps can be subdivided into process sub-steps in which tissue samples are exposed to the aforesaid reagents having different degrees of purity.

Once these process steps have been executed in a tissue processor workflow, a process of cleaning the retorts 21A and 21B is carried out using the aforesaid, or further reagents; for example by performing the aforesaid process steps in reverse order without tissue samples in retorts 21A and 21B. The tissue processor 20 includes a cabinet 23 having two drawers for containers 25 containing the reagents that are necessary for various processes, including the fixing process, the dehydration process, and/or the cleaning process.

A work area is provided on a desktop of the tissue processor 20, as well as a display 27. It will be appreciated that the CPU 11 and memory 24 are provided by the tissue processor 20 to control the treatment processes for the tissue samples according to the tissue processor workflow and to monitor the tissue samples being processed. The display 27 is configured by the CPU 11 to display information indicative of the sample record 17 to a user of the tissue processor 20. For example the sample record 17 is shown as a collated report on the display 27 that can be filtered by the user.

The retorts 21A and 21B are embodied in the tissue processor 20 as a sealable chamber having an opening for receiving the tissue samples in a basket and is shown in a closed position. Inside one of the retorts 21A, various reagents (e.g. paraffin, which is important for the infiltration process) can act on the tissue samples by pressure, vacuum, and or temperature. The interior of the retort 21A is connected via a valve arrangement to lines from the reagent containers 25 via electrically controllable valves. For example, one line is connected via a valve to the contents of the retort 21A so that, under the control of the valve, liquid paraffin is delivered from a corresponding reagent container 25. Further lines connect to further reagent containers 25 for reagents required for the fixing process, the dehydration process, and/or the clearing process, etc. In addition, another line is connected to a distributor that distributes liquid paraffin under the control of valves. The paraffin can be contained in a supply station for paraffin or one of the reagent containers 25. In a further embodiment, the distributor is connected to lines that connect it to containers 25 containing liquid paraffin with an increasing degree of purity.

In the embodiment, the lines are also heated, as is the distributor and, depending on the reagent used, the valve arrangements as well, in order to ensure that the paraffin is always kept in a liquid state, e.g. at 65° C., and does not solidify during operation. The same is also true of retorts 21A and 21B and its parts, and of the supply station and some of the containers.

Sensors 29 are arranged on the tissue processor 20 to sense properties of the tissue sample being processed (see, for example, FIG. 2). These sensors 29 are associated with each of the plurality of processing stations 22, such as the retorts 21A and 21B, in the tissue processor 20 and are arranged to sense the properties of the tissue sample as it processed.

For example, some of the sensors 29 are located between reagent containers 25 and the retorts 21A and 21B, and between the distributor and its valves. Another sensor is provided for acquisition of a measured value that is representative of a characteristic property of the paraffin; in particular of a degree of purity of the paraffin that is currently flowing through the line. It is thus possible, as the paraffin is being pumped to the retorts 21A and 21B and back to the containers 25 to ascertain the different degrees of purity of the paraffin currently being used, before and after treatment of the tissue samples. In this example, the sample record includes the tissue processor workflow data indicative of the step of processing using paraffin and details of the purity of the paraffin that was used in this processing step. This information in the sample record 17 could be used to audit, troubleshoot, check instrument usage and maintenance, check reagent usage and re-order reagents for inventory management and reagent usage optimization.

Examples of sensors 29 include an optical sensor configured to sense turbidity or coloration of the paraffin—the paraffin can be treated with a colouring agent in order to ascertain its degree of purity. Also, using this type of sensor, it is possible to ascertain a density or a conductivity of the paraffin, as a function of which the degree of purity can then be ascertained.

The next steps in the fixing process involve pumping successive process media from other reagent containers 25 via connectors to the retorts 21A and 21B by, for example, applying pressure to these reagent containers 25. These reagent containers 25 contain the corresponding process media at different degrees of purity. Other ones of the sensors 29 of the tissue processor 20 thus include a density sensor and a pressure sensor to sense the density of the process medium that is currently flowing to the retorts 21A and 21B. The degree of purity of the process medium can be determined as a function of its density. The density sensor and the pressure sensor are thus used for acquiring a measured value that is representative of the degree of purity of the process medium. The density sensor is suitable in particular for ascertaining the degree of purity of alcohol or xylene used in this processing step.

Also, the process media that are stocked in the reagent containers 25 encompass, for example, fixing reagents, in particular alkaline fixing reagents, for example formalin; dehydration reagents, in particular alcohols, in particular ethanol; intermedia, for example isopropanol or aromatic compounds, in particular xylene; and/or cleaning reagents, in particular distilled water. In addition, the fixing reagents, dehydration reagents, and/or intermedia can also be used for cleaning and, in this context, can also be referred to as cleaning reagents. One or more other sensors 29 can also be provided for sensing characteristic properties of all the process media used. These characteristic properties can be measured using the following, but not limited to, sensors: a photosensor, a conductivity sensor, and a pH sensor.

Figure 6:
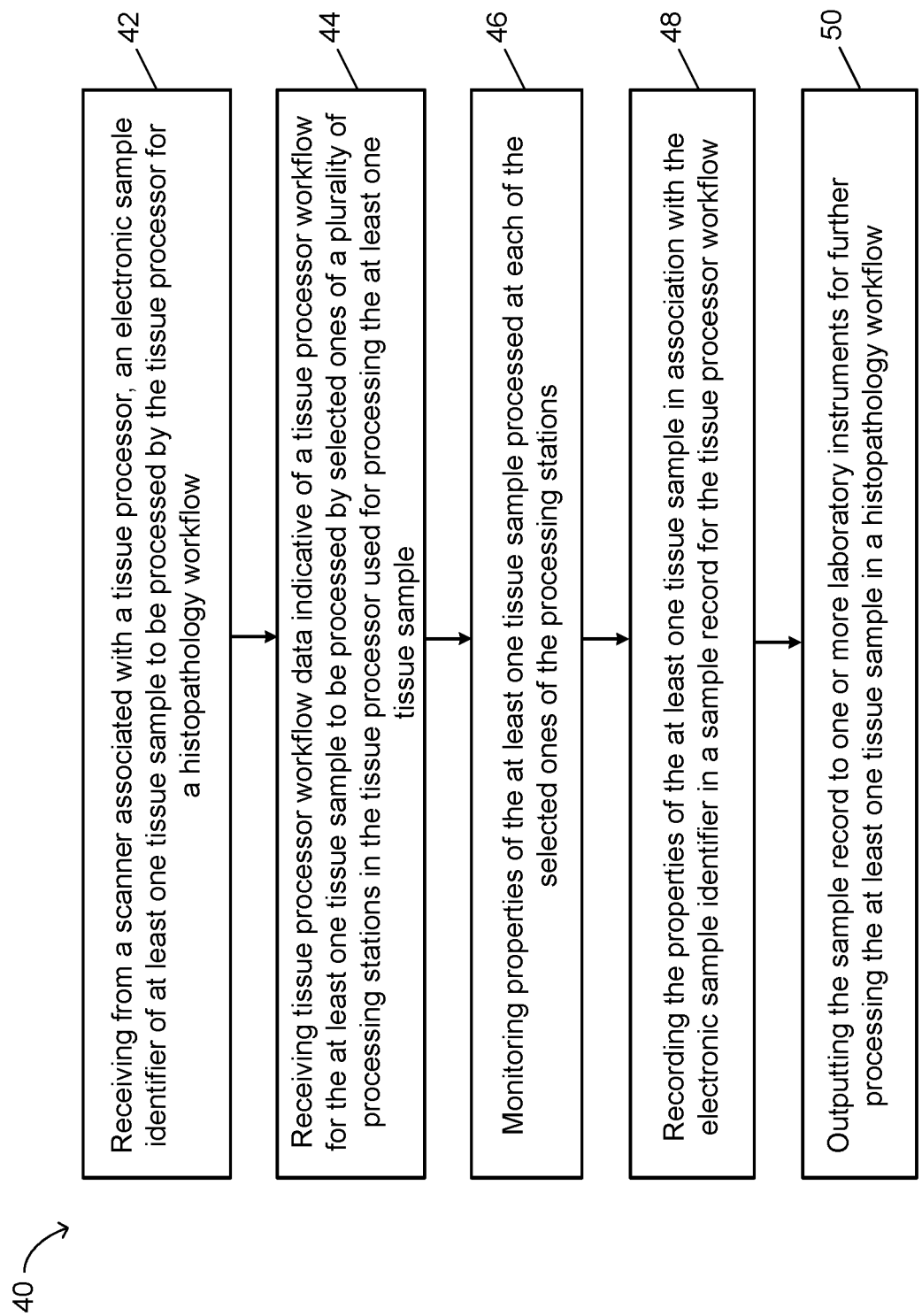
FIG. 6 is a flow chart of a method of monitoring tissue samples to be processed by a tissue processor for a histopathology workflow according to an embodiment of the present invention.

Referring now to FIG. 6, there is shown a summary of a method 40 of monitoring tissue samples to be processed by a tissue processor for a histopathology workflow, the method including: receiving 42 from a scanner associated with the tissue processor, an electronic sample identifier of at least one tissue sample to be processed by the tissue processor; receiving 44 tissue processor workflow data indicative of a tissue processor workflow for the at least one tissue sample to be processed by selected ones of a plurality of processing stations in the tissue processor used for processing the at least one tissue sample; monitoring 46 properties of the at least one tissue sample processed at each of the selected ones of the processing stations; recording 48 the properties of the at least one tissue sample in association with the electronic sample identifier in a sample record for the tissue processor workflow; and outputting 50 the sample record to one or more laboratory instruments for further processing the at least one tissue sample in a histopathology workflow.

Further aspects of the method will be apparent from the above description of the system 10 and the tissue processor 20. Persons skilled in the art will also appreciate that the method could be embodied in program code. The program code could be supplied in a number of ways, for example on a memory of the tissue processor 20, or on a tangible computer readable medium, or communicated as a data signal or file for the tissue processor 20.

It is also to be understood that various alterations, additions and/or modifications may be made to the parts previously described without departing from the ambit of the present invention, and that, in the light of the above teachings, the present invention may be implemented in software, firmware and/or hardware in a variety of manners as would be understood by the skilled person.

It is also to be understood that the following claims are provided by way of example only, and are not intended to limit the scope of what may be claimed in any future application. Features may be added to or omitted from the claims at a later date so as to further define or re-define the invention or inventions.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

Where any or all of the terms "comprise", "comprises", "comprised" or "comprising" are used in this specification (including the claims) they are to be interpreted as specifying the presence of the stated features, integers, steps or components, but not precluding the presence of one or more other features, integers, steps or components.

The invention claimed is:

1. A system for monitoring tissue samples to be processed by a tissue processor for a histopathology workflow, the system including:
    a scanner associated with the tissue processor arranged to scan an electronic sample identifier of at least one tissue sample to be processed by the tissue processor;
    an input module arranged to receive tissue processor workflow data indicative of a tissue processor workflow for the at least one tissue sample to be processed by selected ones of a plurality of processing stations in the tissue processor used for processing the at least one tissue sample;

a monitoring module arranged to monitor properties of the at least one tissue sample processed at each of the selected ones of the processing stations and to record the properties of the at least one tissue sample in association with the electronic sample identifier in a sample record for the tissue processor workflow; and an output module arranged to output the sample record to one or more laboratory instruments for further processing the at least one tissue sample in a histopathology workflow.

2. The system according to claim 1, wherein the sample record further includes, in association with the electronic sample identifier, the tissue processor workflow data indicative of the tissue processor workflow for the at least one tissue sample.

3. The system according to claim 2, wherein the sample record further includes, in association with the electronic sample identifier, expected properties of the at least one tissue sample based on the tissue processor workflow for the at least one tissue sample.

4. The system according to claim 1, the system further including one or more sensors associated with each of the plurality of processing stations in the tissue processor arranged to sense said properties of the at least one tissue sample being processed.

5. The system according to claim 4, wherein the properties of the at least one tissue sample comprise an indication of a level of purity of a media used in processing the at least one tissue sample.

6. The system according to claim 1, wherein the at least one tissue sample to be processed by the tissue processor is provided in a cassette, and the electronic sample identifier includes a cassette identifier.

7. The system according to claim 6, wherein the cassette is provided in a basket, and the electronic sample identifier further includes a basket identifier.

8. The system according to claim 7, wherein the at least one sample is associated with the basket identifier at grossing of the at least one sample.

9. The system according to claim 1, wherein the electronic sample identifier includes a barcode tag.

10. A tissue processor for processing tissue samples for a histopathology workflow, the tissue processor including:
a scanner arranged to scan an electronic sample identifier of at least one tissue sample to be processed by the tissue processor;
a plurality of processing stations arranged to process the at least one tissue sample;
an input module arranged to receive tissue processor workflow data indicative of a tissue processor workflow for the at least one tissue sample to be processed by selected ones of the plurality of processing stations;
a monitoring module arranged to monitor properties of the at least one tissue sample processed at each of the selected ones of the processing stations and to record the properties of the at least one tissue sample in association with the electronic sample identifier in a sample record for the tissue processor workflow; and an output module arranged to output the sample record to one or more laboratory instruments for further processing the at least one tissue sample in a histopathology workflow.

11. The tissue processor according to claim 10, wherein the sample record further includes, in association with the electronic sample identifier, the tissue processor workflow data indicative of the tissue processor workflow for the at least one tissue sample.

12. The tissue processor according to claim 11, wherein the sample record further includes, in association with the electronic sample identifier, expected properties of the at least one tissue sample based on the tissue processor workflow for the at least one tissue sample.

13. The tissue processor according to claim 10, the tissue processor further including one or more sensors associated with each of the plurality of processing stations in the tissue processor arranged to sense said properties of the at least one tissue sample being processed.

14. The tissue processor according to claim 10, wherein the at least one tissue sample to be processed by the tissue processor is provided in a cassette, and the electronic sample identifier includes a cassette identifier.

15. The tissue processor according to claim 14, wherein the cassette is provided in a basket, and the electronic sample identifier further includes a basket identifier.

16. The tissue processor according to claim 15, wherein the at least one sample is associated with the basket identifier at grossing of the at least one sample.

17. The tissue processor according claim 10, wherein the electronic sample identifier includes a barcode tag.

18. The tissue processor according to claim 10, further including a display, wherein information indicative of the sample record is displayed on the display to a user of the tissue processor.

19. A method of monitoring tissue samples to be processed by a tissue processor for a histopathology workflow, the method including:
receiving from a scanner associated with the tissue processor, an electronic sample identifier of at least one tissue sample to be processed by the tissue processor;
receiving tissue processor workflow data indicative of a tissue processor workflow for the at least one tissue sample to be processed by selected ones of a plurality of processing stations in the tissue processor used for processing the at least one tissue sample;
monitoring properties of the at least one tissue sample processed at each of the selected ones of the processing stations;
recording the properties of the at least one tissue sample in association with the electronic sample identifier in a sample record for the tissue processor workflow; and
outputting the sample record to one or more laboratory instruments for further processing the at least one tissue sample in a histopathology workflow.

* * * * *